United States Patent [19]

Ettinger et al.

[11] Patent Number: 5,293,414
[45] Date of Patent: Mar. 8, 1994

[54] NUCLEAR RESONANCES IN ACTIVATION ANALYSIS, AND PARTICULARLY, ITS APPLICATION TO DETECTION OF NITROGEN BASED EXPLOSIVES IN LUGGAGE

[75] Inventors: Kamil V. Ettinger; Joseph H. Brondo, both of East Hampton, N.Y.

[73] Assignee: Scientific Innovations, Inc., Wainscott, N.Y.

[21] Appl. No.: 635,537

[22] Filed: Mar. 4, 1991

Related U.S. Application Data

[63] Continuation-in-part of Ser. No. 349,326, May 8, 1989, Pat. No. 5,040,200.

[51] Int. Cl.$^5$ .............................................. G01N 23/04
[52] U.S. Cl. .................................. 378/88; 378/83; 378/86; 378/57
[58] Field of Search .................. 378/86, 83, 88, 57, 378/51, 53

[56] References Cited

U.S. PATENT DOCUMENTS

| | | |
|---|---|---|
| 3,171,961 | 3/1965 | Yule et al. |
| 3,780,294 | 12/1973 | Sowerby ........................... 250/364 |
| 5,040,200 | 8/1991 | Ettinger et al. ........................ 378/88 |

FOREIGN PATENT DOCUMENTS

| | | |
|---|---|---|
| 0218240 | 10/1986 | European Pat. Off. |
| 0354326 | 6/1989 | European Pat. Off. |
| 0358237 | 9/1989 | European Pat. Off. |
| 0455515 | 5/1991 | European Pat. Off. |

*Primary Examiner*—Paul M. Dzierzynski
*Assistant Examiner*—Don Wong
*Attorney, Agent, or Firm*—Scully, Scott, Murphy & Presser

[57] ABSTRACT

The invention relates to an apparatus and method for detecting the presence of an element of interest within an object. The object is positioned where a beam of gamma rays of the required energy are directed to be scattered by the element of interest. The gamma rays are provided by excited atoms of the element of interest. The excited atoms result from the reaction of hydrogen or heavier ions and a suitable target. The excited atoms deexcite, releasing gamma rays which are scattered by the element of interest within the object. The scattered gamma rays are detected, output signals are produced, processed and analyzed to determine the amount of the element of interest within the object. A preferred embodiment relates to the detection of nitrogen-based explosives in luggage.

28 Claims, 6 Drawing Sheets

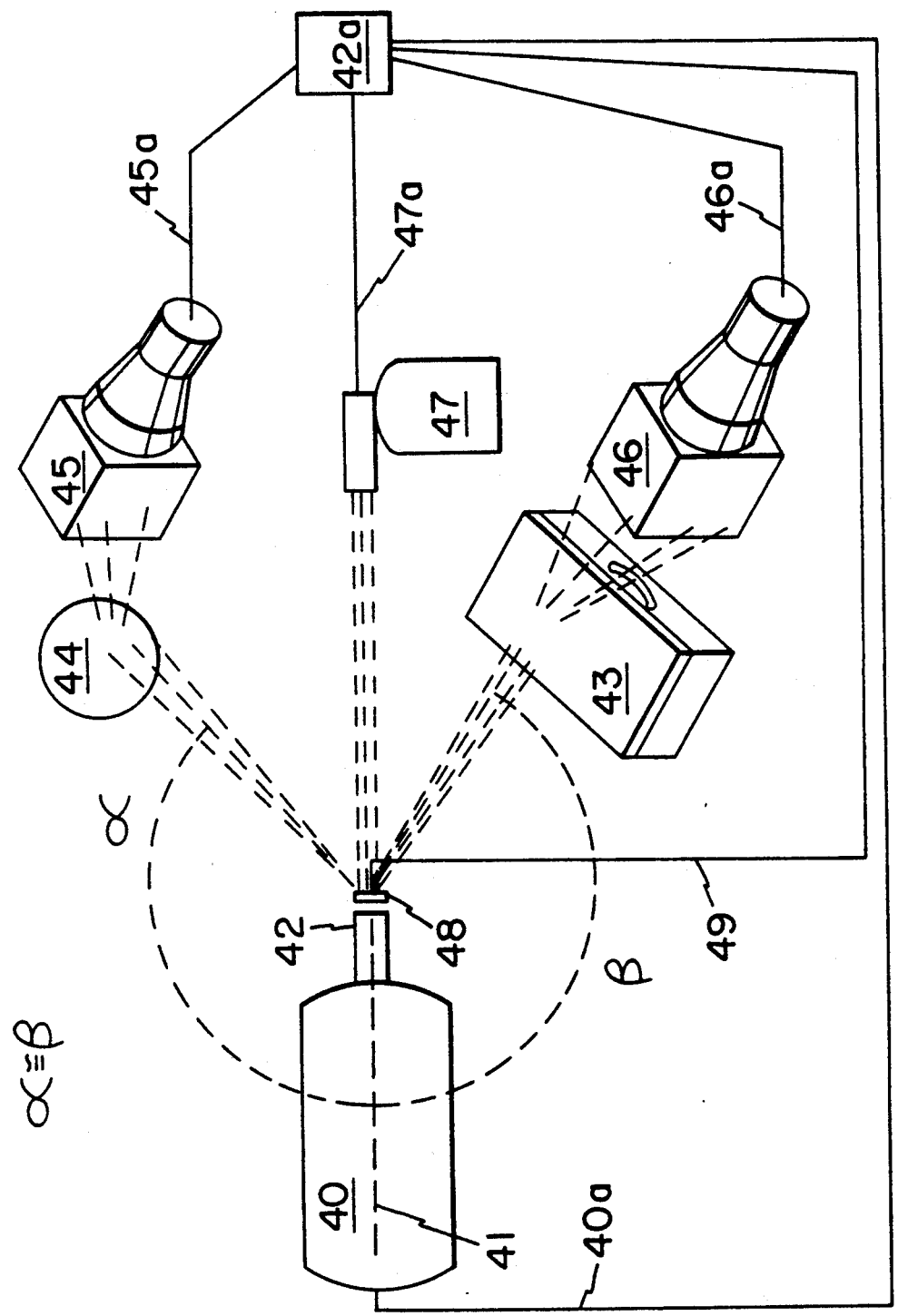

NUCLEAR RESONANCES IN ACTIVATION ANALYSIS, AND PARTICULARLY, ITS APPLICATION TO DETECTION OF NITROGEN BASED EXPLOSIVES IN LUGGAGE

This application is a continuation-in-part of application Ser. No. 349,326, filed May 8, 1989 now U.S. Pat. No. 5,040,200.

BACKGROUND OF THE INVENTION

1. Field of the Invention

This invention is directed to an apparatus and method for scanning an object for an element of interest and especially for nitrogen in nitrogen-based explosives. More particularly, the invention is directed to an apparatus utilizing gamma-gamma resonance which causes gamma rays to be scattered by the element of interest that is detected and analyzed to provide a representation of the concentration of the element of interest contained within the object.

The subject apparatus and method finds further application in drug detection, body composition, industrial applications, substance detection, food analysis and medical applications including veterinary medicine.

This invention is further directed to a gamma ray detector utilizing a nuclear resonance fluorescence filtering element.

2. Description of the Prior Art

The technique of nuclear resonance fluorescence has been employed for elemental and isotope analysis, both qualitative and quantitative. Particular applications include devices for well logging, borehole prospecting, on-stream analysis and the analysis of planet surfaces.

A significant threat to human life and property exists when an explosive device is concealed in luggage or parcels brought into buildings, aircraft, etc. As a result, there is a need by both the public and private sector of the country for a reliable technique for the detection of such explosive devices. As the threat of terrorist activities throughout the world, especially in airports, has increased, the demand for an efficient and practical device for scanning luggage to determine the presence of explosives has intensified.

It is well known that explosives may be detected by sensing the amount of nitrogen in the object being examined. One technique of detecting nitrogen is by the subject method of nuclear resonance fluorescence (nuclear resonance scattering).

U.S. Pat. No. 3,171,961 relates to a method of well logging by nuclear resonance fluorescence for the detection of a given nucleus, particularly carbon and oxygen. Nuclear reactions are described as a method of providing radiation wherein a bombarding nucleon from an accelerator is employed to produce an excited nucleus of the atoms being detected in a geological setting.

U.S. Pat. No. 2,726,838 relates to the use of the reaction between accelerated elementary charged particles and target means to provide a monoenergetic neutron source for bombarding the analyzed object, thereby inducing a radioactive response which is detected. The preferred reaction is the reaction of deuterons with tritium.

U.S. Pat. No. 3,780,294 relates to the use of nuclear fluorescence for elemental analysis. The use of an accelerator to provide bombarding particles for nuclear reactions to produce gamma rays is discussed wherein the inventor indicates that the Doppler broadening may be too great and, therefore, would not provide a good method for the production of gamma rays.

SUMMARY OF THE INVENTION

The present invention is directed to an apparatus and method for scanning an object for an element of interest and determining the concentration of the element in the object. An accelerator provides hydrogen or heavier ions, preferably hydrogen or deuterium, directed at a target to produce excited atoms of the element of interest. The excited atoms deexcite to provide a beam of gamma rays of the required energy. The object is positioned within the beam of gamma rays. The gamma rays are scattered by the element of interest within the object. The resonantly scattered gamma rays are then detected and output signals produced. The output signals are representative of the amount and energy of the gamma rays, thereby allowing determination of the presence and amount of the element of interest within the object being scanned.

The apparatus and method are applied to a variety of objects for analysis thereof. The detection of nitrogen in explosives represents a preferred embodiment of the subject invention. Further embodiments include the detection of drugs in an object, body composition determination, industrial applications, substance detection, food analysis and medical and veterinary examination.

This invention further relates to a gamma detector utilizing a nuclear resonance fluorescence filtering element comprising nuclei having the same nuclear energy levels as energies of the gamma rays to be detected. The nuclear resonance fluorescence scatterer may be active or passive. In the active mode, the nuclear resonance fluorescence scatterer may operate as the radiation detector itself or as a part of it.

BRIEF DESCRIPTION OF THE DRAWINGS

FIG. 4 is a schematic illustration of beam intensity and beam energy stabilization in gamma-gamma analysis.

DETAILED DESCRIPTION OF THE INVENTION

Figure 1:
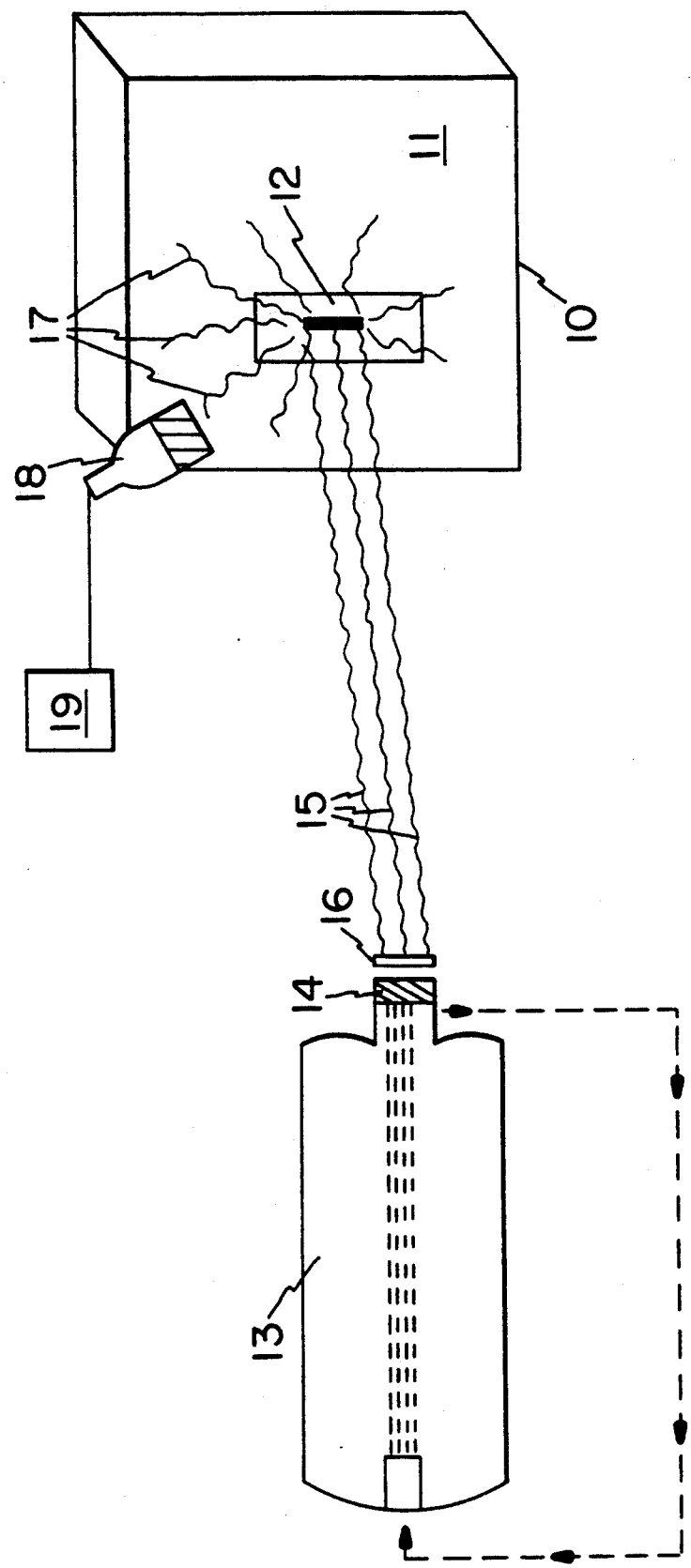
FIG. 1 is a schematic illustration of the apparatus for detecting the presence of an element of interest, in accordance with the present invention.

The gamma-gamma resonance method is an application of the phenomenon known as Nuclear Resonance Scattering or Nuclear Resonance Fluorescence. In this technique, the gamma radiation of properly and precisely chosen energy is used to excite the corresponding energy levels in the analyzed object, which plays the role of the scatterer. The resonantly scattered radiation is then detected and analyzed.

The phenomenon of nuclear resonant fluorescence is a particular case of elastic scattering of photons from nuclei, with the photon energy and the energy of the nuclear level exactly matching one another. This process, which is characterized by a very large cross section in comparison with other photon scattering processes, has been used almost exclusively for the determination of nuclear lifetimes and has been applied to the activation analysis of minerals and the determination of the concentration of some elements, in vivo, in man. In the activation analysis applications, the nuclear resonance scattering has been used as a method of excitation of nuclear levels in analyzed objects.

A gamma ray, emitted by a nucleus initially at rest, has an energy only approximately equal to the difference between the energy levels involved in the radiative transition. In fact, the emitted quantum is lacking the amount of energy taken by the recoiling nucleus.

Photons are characterized by their energy $E_\gamma$ and their momentum $P_\gamma$, which are related through $$P_\gamma = E_\gamma/c \qquad (1)$$

where c is the velocity of light.

Thus, if an excited nucleus, initially at rest but free to recoil in the laboratory frame, deexcites by emission of a gamma ray, the conservation of momentum requires that this nucleus should recoil in the direction opposite to that of the photon.

The recoil velocity, V, is determined by the momentum conservation:

$$MV = -E_\gamma/c \qquad (2)$$

where M is the mass of nucleus.

The energy balance gives:

$$E = MV^2/2 + E_\gamma \qquad (3)$$

where E is the energy of the radiative transition. It can be also written as:

$$E = E_\gamma + E_\gamma^2/2Mc^2 \qquad (4)$$

The energy of the emitted gamma ray is thus slightly less than the transition energy; the difference, expressed in practical units, is:

$$E - E_\gamma = (5.37 \times 10^{-4}) E_\gamma^2/A \text{ [in MeV]} \qquad (5)$$

where A is the atomic number of the emitting nucleus. Since E is not very different from $E_\gamma$, the following approximation can be made:

$$E - E_\gamma = (5.37 \times 10^{-4}) E^2/A \qquad (6)$$

A similar phenomenon is observed in gamma ray absorption, i.e. the same amount of energy is transferred to the recoiling nucleus. The photon energy, which is necessary to excite a transition E, is:

$$E_\gamma = E + E^2/2Mc^2 \qquad (7)$$

Consequently, the photon corresponding to the transition energy E is off resonance by an amount $E^2/Mc^2$. In other words, the nucleus is not capable of absorbing its own radiation if the difference of both recoils, i.e. at the moment of emission and at the moment of absorption, is not compensated in some way.

When a gamma ray is emitted by a nucleus, which is moving with respect to the detector or scatterer, a small energy shift is observed. This effect is called the Doppler effect in analogy with the equivalent phenomenon observed in acoustics. If v is the nucleus velocity before the act of emission, we have the relationship:

$$E_\gamma = E_\gamma'[1 + (v/c)\cos v] \qquad (8)$$

where $v$ is the angle between the direction of recoil and the direction of gamma quantum. The use of the Doppler effect has been the principal method of compensation of energy disparity between the photon and appropriate nuclear level. It has been employed in the form of imparting motion of emitters and scatterers in respect of each other by direct mechanical motion, by heating of the emitter or absorber or by employing recoil of the parent nucleus in processes of beta decay briefly preceding the emission of gamma ray photon. A similar Doppler energy compensation can be attained by means of nuclear collisions in which the exciting photons are generated.

The energy deficit arising from the recoil, associated with absorption, can be compensated by exciting the primary emitters with fast charged particles through the process of inelastic scattering. In this process, the nucleus acquires some of the kinetic energy of the incoming projectile; and the degree of compensation depends upon the angle between the movement of the struck nucleus and the direction in which the quantum from deexcitation is emitted.

Similarly, it is possible to obtain the compensating shift in gamma ray energy in neutron capture processes. It is known that when epithermal neutrons are captured into very short lived, energetically broadened states, the energies of some of the emitted gamma rays are slightly higher than those appearing in the thermal neutron capture spectra. Neutron capture of a non-zero energy neutron is also a non-elastic collision; and, thug in addition, the capturing nucleus exhibits a recoil, because of the need to preserve the momentum.

The method of resonant scattering (NRF) has been used in the past in-activating analysis, but the method of producing the exciting radiation represents a novelty. This method is based on exploitation of the phenomenon of charged particle resonance, a different resonance effect in nucleus from the above described resonant scattering of gamma quanta.

The usual nuclear reaction is characterized by the interaction of the incident particle with a stationary target nucleus, neglecting the thermal motion of the latter. As a consequence of the interaction, a nuclear reaction may take place; and the incident particle may be scattered, captured, disintegrated (stripped) or may be aggrandized by picking up a nucleon from the target. The target nucleus, apart from a recoil, may be excited whether transformed into another species or not. Resonance takes place when the system composed of incident particle and the target nucleus has energy equal to the energy level of the compound nucleus formed. An excited nucleus may stay in the metastable state for some time, or may deexcite almost instantaneously with an emission of gamma quanta or other particles. In fact, there may be more than one mode of decay from the excited state. The cross sections for these reactions are a function of energy; and, in general, can be classified as resonant or non-resonant with the borderline between these two types diffuse and uncertain. Examples of non-resonant reactions are Coulomb and potential scattering and so called direct reactions, like stripping (Oppenheimer-Phillips reaction is a special case of these), or pick up. The term "resonant reactions" is used for processes in which the cross section exhibits pronounced maxima and minima as the energy of the incident particle is varied. From the point of view of their proposed use in activation analysis, the important numerical parameters of resonant reaction, called sometimes simply "resonances", are energies of the projectile, energies of excited levels, energies of emitted gamma rays or charged particles, cross sectioned at the peak of the resonance (barns), or an integral of cross sections taken over the area of resonance (barns×eV) and the resonance width (eV).

The scanning apparatus of the present invention is schematically illustrated in FIG. 1, in a preferred embodiment for scanning luggage. The apparatus generally includes a housing 10 having a cavity 11 for receiving an object 12 to be scanned. The housing may include a means for transporting the object 12 through the cavity 11. Accelerator 13 provides hydrogen or heavier ions, preferably hydrogen or deuterium ions, directed at a target 14 to provide excited atoms of the element of interest which deexcite and, thereby, produce primary gamma rays, which are collimated by collimator 16. The collimated gamma rays 15 are of the required energy to be resonantly scattered by the element of interest within the cavity 11. The resonantly scattered gamma rays 17 are observed by detector 18, which produce output signals representative of the energy of the gamma rays 17. The angles between the beam of charged particles inside the accelerator 13 and the beam of collimated gamma rays 15, in addition to the angle between the collimated gamma rays 15 and the resonantly scattered gamma rays 17 reaching the detector 18, may differ. Means 19 processes and analyzes the output signals for determining the amount of the element of interest. Detector 18 observes the resonantly scattered gamma rays 17 preferably at an angle of 45° to 175°, most preferably larger than 90 degrees from the axis of bombardment at which the primary gamma rays 15 interact with the object 12 being scanned.

The incident particle interacts with the target nucleus to form a compound nucleus. The energy of the compound nucleus, neglecting the recoil, is equal to the sum of the binding energy of the projectile within the target plus the kinetic energy in the center of the mass of the projectile. If this excitation energy corresponds to one of the energy levels of the compound nucleus, the resonance takes place; and the corresponding cross section for the production of gamma rays shows a maximum. The intensity of gamma rays arising from the deexcitation reaches a maximum. Examples of such charged particle resonances are the reactions C-13 (p,gamma) N-14 at an energy of 1747.6 keV and C-12 (d, gamma) N-14 at an energy of approximately 2500 keV. The (p,gamma) reactions were tabulated in J. W. Butler "Report of the Naval Research Laboratory", NRL-5282 (1959). More recent data on charged particle resonances can be found in "Nuclear Data Sheets" and also in the compilations of nuclear energy levels published regularly by Endt and Ajzenberg-Selove in "Nuclear Physics", ser. A.

Figure 2A:
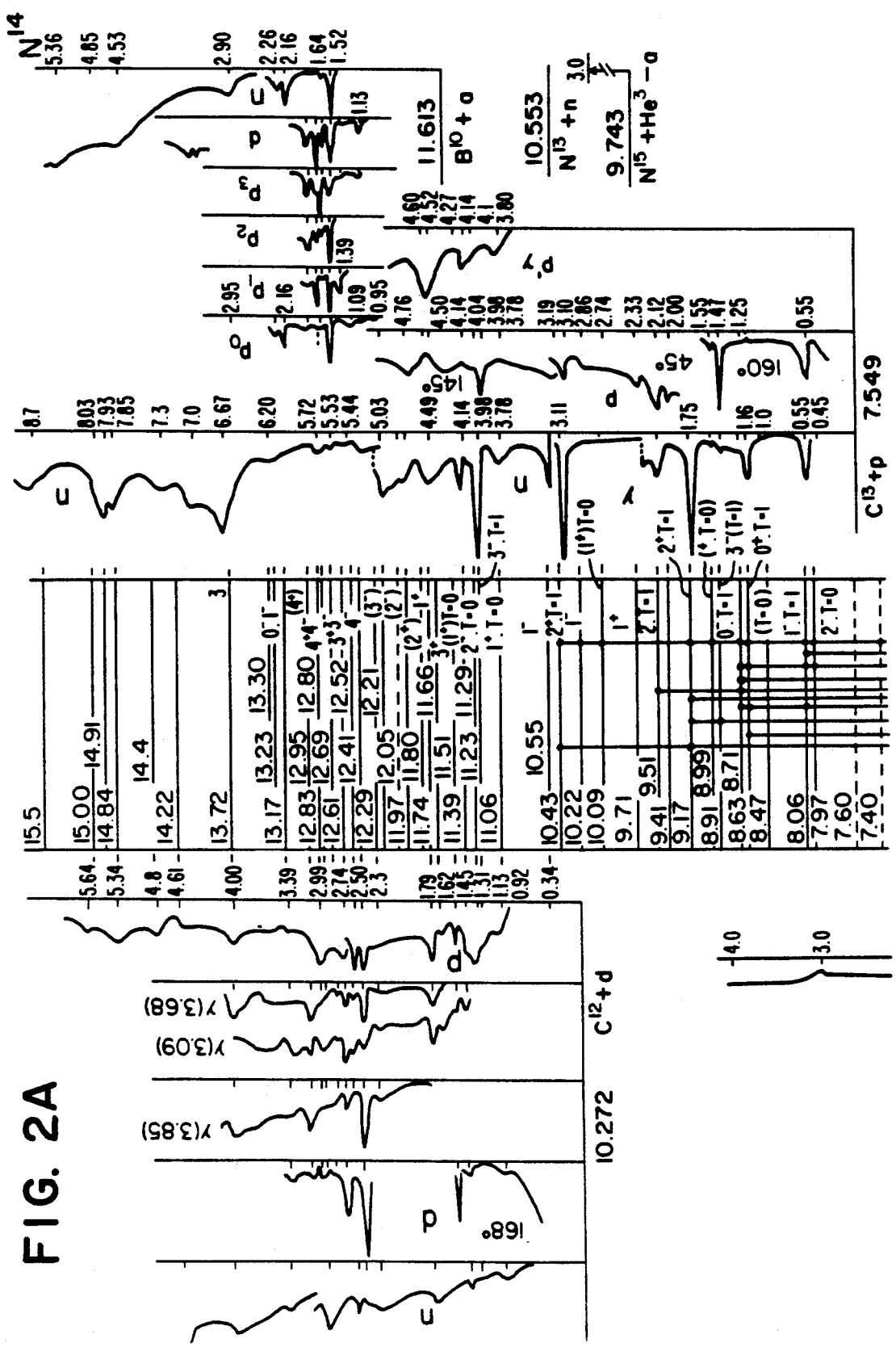
FIGS. 2a–2b are nuclear resonance schemes of charged particle resonances for N-14.
Figure 2B:
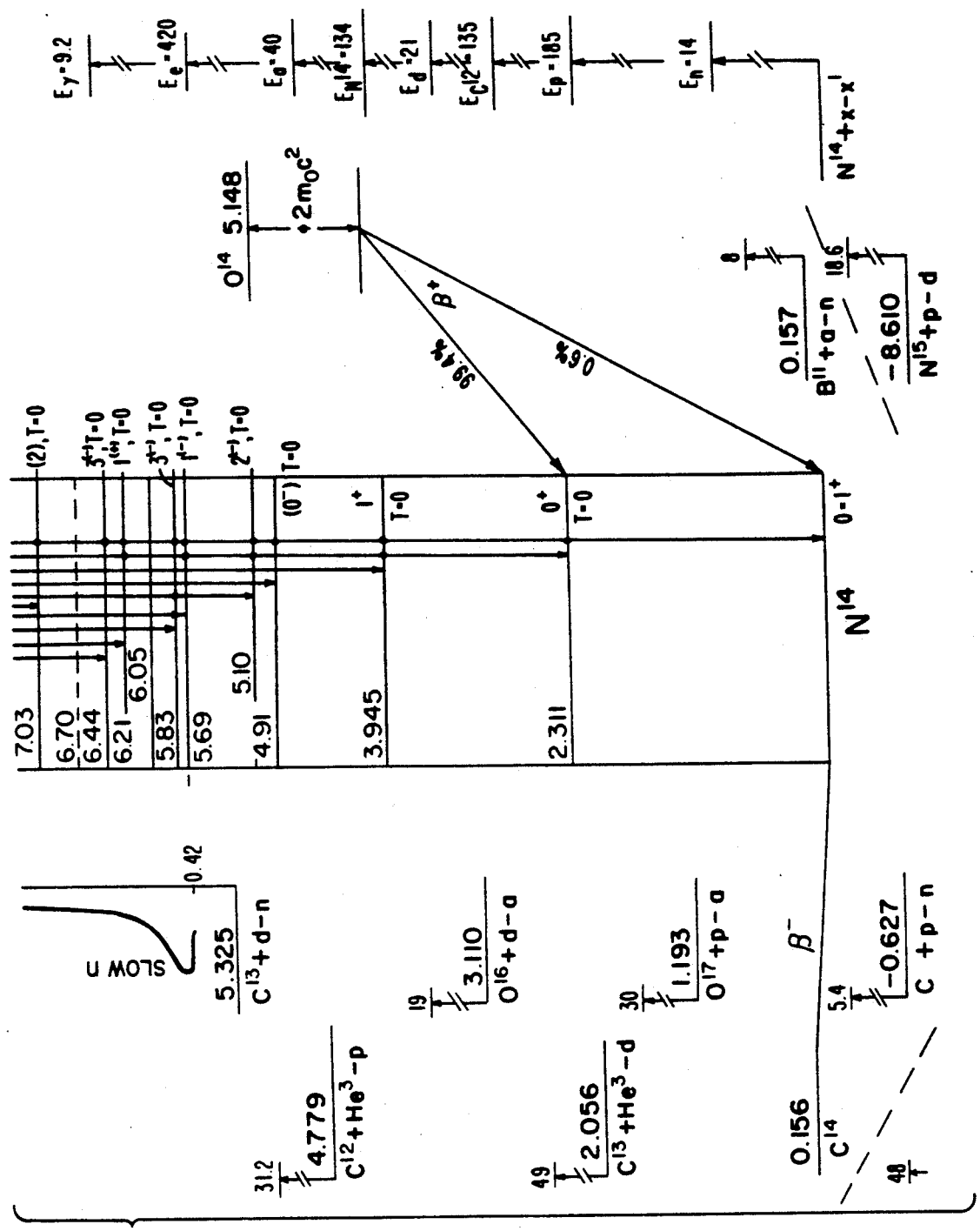

An example of nuclear level scheme, with an indication of charged particle resonance for N-14 from "Nuclear Data Tables", is shown in FIG. 2. The vertical lines show an approximate shape of the dependence of the reaction cross section upon the energy of proton or deuteron projectile. The gamma transitions take place between the levels of final nucleus, and their intensities depending upon the probabilities of various transitions. The resonances at 1747 keV and 550 keV for C-13+p and the resonance at approximately 2500 keV for C-12+d are clearly recognizable. Resonances, in which gamma rays are being produced and which can be utilized for activation analysis, also include reactions with alpha particles and with other heavy ions; even including those in which some heavy charged particles are reemitted.

The gamma rays emitted in these resonances can be used for excitation of the scatterer (analyzed object) in the activation-analysis technique. These gamma rays include transitions to the ground state, unless specifically barred by the selection rules, and thus correspond approximately to the energy levels in the scatterer. The recoil compensation can be provided by the selection of the angle between the charged particle beam and the beam of gamma rays; and if necessary, the target can be provided in a gaseous form, to take advantage of the "in-flight" Doppler shift.

While most of the attention is on the three principal elements of organic matter (carbon, oxygen and nitrogen) the technique of gamma-gamma excitation is, however, fairly general; and any of the resonances can be used with an appropriate selection of the target, projectile and bombarding particle energy. The only elements which cannot be excited by this method are hydrogen and helium. It should, however, be kept in mind that with an increase in the atomic number of the target element, the energy of the projectiles must be increased so that they can penetrate the Coulomb barrier.

The main requirements for the charged particle source are stability of the energy of projectiles striking the target and sufficient intensity of the beam to provide an adequate photon flux, which in turn depends upon the cross sections of the reaction in use. The energy stability of the charged particle beam should be such that the production of the gamma rays corresponds to the resonant peak of the cross section curve and remains there during the operation of the accelerator. Depending upon the selection of the resonance peak, the width of the resonance may be of an order of tens of electronvolts or even much less. Furthermore, there is some degree of dependence of the energy of resonant gamma rays on the exact value of charged particles energy, within the resonance peak. For those resonances in which this dependence is particularly prominent, stabilization of the charged particle energy is needed to maintain high intensity of gamma ray production and to maintain the energy of gamma rays within the resonance curve of corresponding nuclear energy level in the scatter.

The beam energy stabilization requires a beam energy sensor, signal processing device and the effector (controller) which acts upon the accelerator, beam transport or beam target. The present proposal is concerned with the beam energy sensor, which provides means for stabilization of the accelerator particle beam energy precisely at the value or values which are required for efficient analysis, i.e. at the resonance peak of charged particle resonance.

Figure 3:
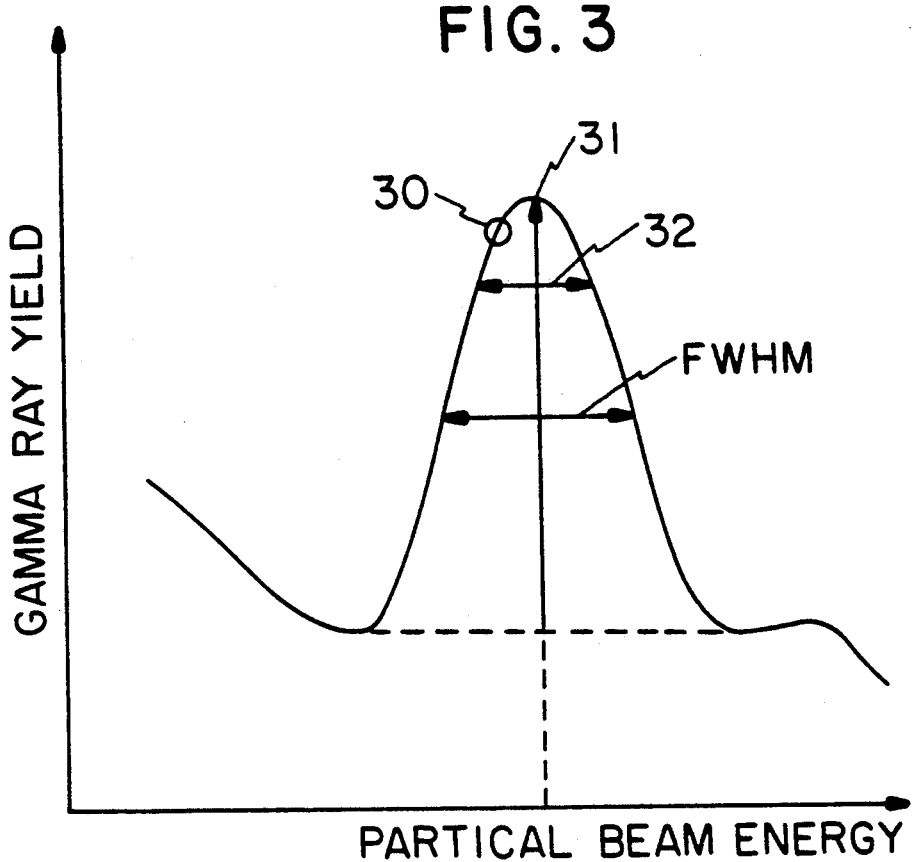
FIG. 3 graphically illustrates astable energy control for charged particle resonance.

The charged particle resonance is a phenomenon observed in nuclear physics, in which during bombardment of nuclei with heavy charged particles, at certain energies of projectiles, the reactions of simple radiative capture, e.g. (p,gamma) or (d,gamma) or radiative capture with emission of a charged particle or neutron, e.g. (p,alpha gamma) or (p, n gamma), etc. are showing a significantly increased yield. The shape of the resonance curves, i.e. yield versus projectile energy, resemble Lorentz resonance curves. A part of a typical gamma ray yield curve from a resonant reaction is shown in FIG. 3.

The FWHM widths of resonance curves vary within very broad limits depending upon the nuclear structure and its spectroscopic properties. For charged particle resonances applied to the needs of activation analysis, one should expect resonance peak widths (FWHM) in the range from a few kiloelectronvolts down to a few electronvolts. The resonance peak of $^{13}C(p, gamma)^{14}N$ at about 1.748 MeV has a FWHM width of about 70 eV. The required stability of the accelerating voltage is about $2 \times 10^{-5}$. This is a difficult, but attainable requirement at the present state of the art. The beam energy sensor simplifies the design of the apparatus.

If the gamma rays produced in the charged particle resonance are to be used for measurement involving Nuclear Resonance Scattering (or Fluorescence), then the width of the scattering level is much smaller than the width of the charged particle resonance. Because the energy of the gamma rays produced in the charged particle resonance varies slightly with the energy of the projectile, a tighter gamma energy control is required in many applications of the gamma-gamma technique then would be required for the maintenance of only the charged particle resonance. Such a degree of control is, to date, not achievable by electronic means, including systems with a bent beam, pair of slits and differential slit current amplification (a useful reference is "Electronic Devices For Electrostatic Accelerators" (in Russian), V. G. Brovtchenko, P. E. Vorotnikov and Yu. D. Moltchanov, Atomizdat Publishing House, Moscow 1968).

The beam energy sensor described herein measures the intensity, i.e. yield, of resonant gamma rays, those which are used for activation analysis. FIG. 4 shows the arrangement of the equipment for gamma-gamma analysis including elements intended to provide control of the beam intensity and beam energy, independently.

The accelerator 40 provides a charged particle beam (about beam axis 41) which strikes the target 42 and, thereby, produces the beam of gamma rays which are collimated by collimator 48. Whatever the angular distribution of the emitted gamma rays with the non-polarized particle beam, the intensity of emitted gammas is symmetrical with respect to the axis coinciding with the charged particles trajectory. Thus, the analyzed object 43, e.g. a piece of luggage, and the reference scatterer 44, receive beams of the same energy. If the angle between the original, i.e. as emitted from the target, and scattered beams are the same for the both the working and reference channels, then the maximization of the reference channel count rate detected by the reference detector 45 is accompanied by the maximization of the working channel count rate detected by working detector 46, as far as the beam energy is concerned.

In general, the count rate in the reference channel will depend not only upon the precise beam energy, but also upon the accelerator current, or more precisely, upon the total gamma ray yield from the target over the spectral area broader than the resonant line. This information is obtained by monitoring the gamma-ray intensity off the peak of interest, in the continuum area, where the intensity is a slowly changing function of beam energy, utilizing for that purpose, the output of the reference detector 45 or an optional second reference detector 47, e.g. germanium detector. If the overall beam intensity has changed, the beam current may need an adjustment. However, the monitoring system will monitor the ratio of total yield to the beam current because this may signify deterioration of the target.

The sensor system simply senses the count rate as a function of projectile beam energy. The projectile energy is varied electronically in a way appropriate for a given accelerator type and may include a device for changing the potential of the target. The applicable control system is an astable type. In this type of working point, i.e. the beam energy, is never constant but moves around the resonance peak.

Referring to the working point 30, as in FIG. 3, the beam energy changes upwards as a result of scanning voltage applied to the control input. The count rate increases, and as long as it increases, the scanning voltage moves the beam energy up. The system recognizes the increase because it calculates the difference between the successive readings of the count rate. In this way, the working point reaches the resonance peak 31 and continues to move to higher energies of the particle beam. However, the count rate starts decreasing as the peak has been passed. Once the electronic system recognizes the decrease, the scan direction is reversed. Arbitrary scan reverse limits 32 are shown in FIG. 3. The working point 30 returns to the peak 31 and continues to move towards lower values of beam energy, with accompanying reduction of the count rate. Once this is recognized, the scan is again reversed, etc. In this way, the working point 30 oscillates around the peak 31. To optimize the sensor system, a filtering is provided so that the direction of the scan is reversed only when a sufficient probability is expected that the peak has been passed.

The signal processing device can be either analog, digital or hybrid. It can use either a hard wired logic or a dedicated processor.

When lower requirements for the energy control are sufficient, there may be no need for a reference scatterer 44; and the optional reference detector 47 can observe the primary beam directly.

The reference scatterer 44 should essentially contain a significant quantity of the same nuclide for which the working channel is analyzing the "analyzed object".

A signal 40a representative of the coarse beam energy, a signal 49 representative of the beam current, a signal 46a representative of the resonantly scattered gamma ray intensity, a signal 45a from the active NRF reference detector and a signal 47a from the optional reference detector are connected to controller 42a.

If the analysis is to be performed for more than one element, the accelerator should have an electronic voltage adjustment and control; and the beam should be able to strike different targets. This function of target switching can be done either mechanically or by a deflection device for the beam operated electrostatically or magnetically.

The type of the accelerator is dictated only by the operational and financial imperatives. Electrostatic and Radio Frequency Quadrupole accelerators are the most obvious types.

All the existent gamma- and X-ray radiation detectors are, so far, wide band devices, i.e. responsive to the quanta in a broad range of energies, limited by the absorption of the detector window on the low energy side and the decreasing detection efficiency on the other, high energy side. This is because the detection of photons is a consequence of their interaction with atomic electrons and, thus, requires only an energy of the order of tens of electron volts to be released inside the detector sensitive volume.

On the other hand, nuclear resonance fluorescence is a nuclear process and requires energies of much higher order, frequently more than 10 MeV. Because of the resonant nature of interaction and, particularly, because of very narrow width of resonances involved, the nuclear resonance fluorescence offers a possibility of narrowing the response of radiation detectors to very narrow energy bandwidths, i.e. an energy filtration.

Figure 5:
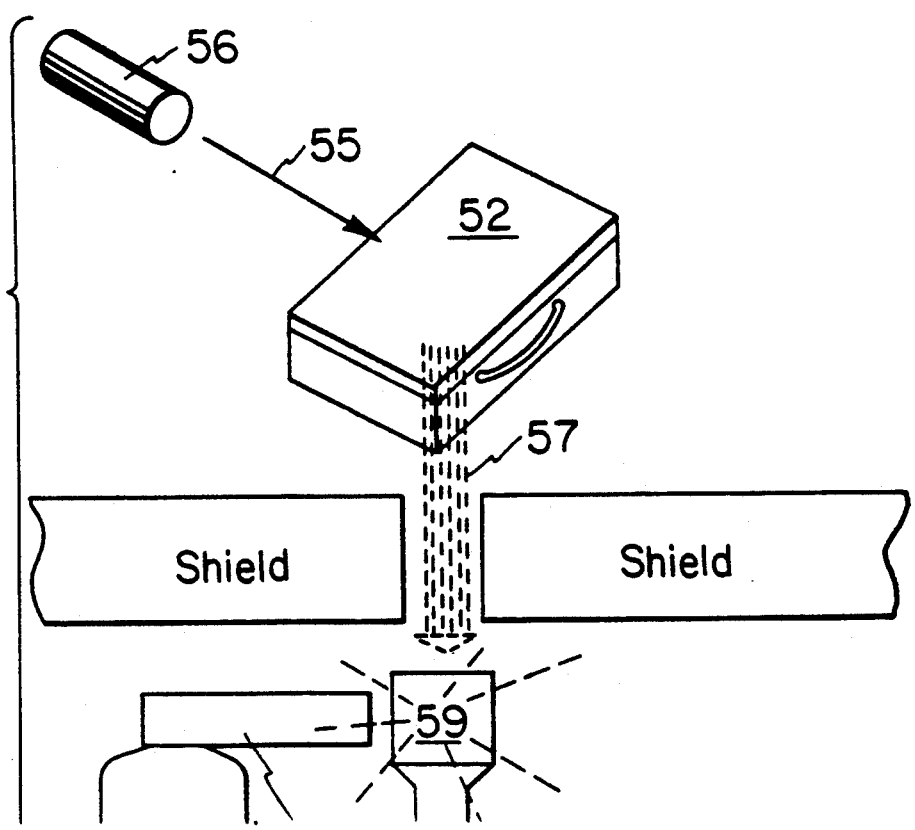
FIG. 5 is a schematic illustration of passive nuclear resonance fluorescence detection, in accordance with the present invention.

This effect can be achieved by incorporating the nuclear resonance fluorescence filtering element into the detector system. The nuclear resonance fluorescence element can be either passive or active. The passive NRF arrangement for a detector of gamma radiation will be discussed first. In such a system the gamma ray flux 57 from the source, i.e. the analyzed object 52, cannot reach the detector 58 directly but only after scattering from the resonance scatterer 59 as in FIG. 5. The analyzed object 52 is exposed to a primary gamma ray beam 55 from a source 56. The way in which the analyzed object 52 is made to emit gamma rays 57 is irrelevant. It may be exposed to gamma rays which are subsequently scattered, it can be exposed to charged heavy particle beams, to electrons or to neutrons. In order that nuclear resonance fluorescence is of value for purpose of activation analysis, the radiation being scattered or emitted by object 52 must contain photons of energies corresponding to those nuclei present in the NRF scatterer 59. The detector system shown in FIG. 5 may also be used in neutron activation analysis wherein the primary gamma ray source 56 and gamma ray beam 55 are replaced by a neutron source and neutron beam, respectively; which cause the element of interest within the analyzed object to emit gamma rays. If neutron capture in the object takes place in nuclei with atomic mass A, the resonance scatterer should contain nuclei of a heavier isotope with atomic mass (Z+1). This is a consequence of fact that following the capture of a neutron by a nucleus of mass Z, the subsequent emission of gamma quantum takes place from an isotope of mass (Z+1). If, on the other hand, the nuclei in the object are excited in the process of inelastic scattering, the atomic mass does not change. In such a case, the same nuclide should be present in the resonance scatterer 59 as the one present in the analyzed object 52. If nuclei in the object 52 are used to resonantly scatter gamma rays, the same nuclei should be present in the NRF scatterer 59.

Figure 6:
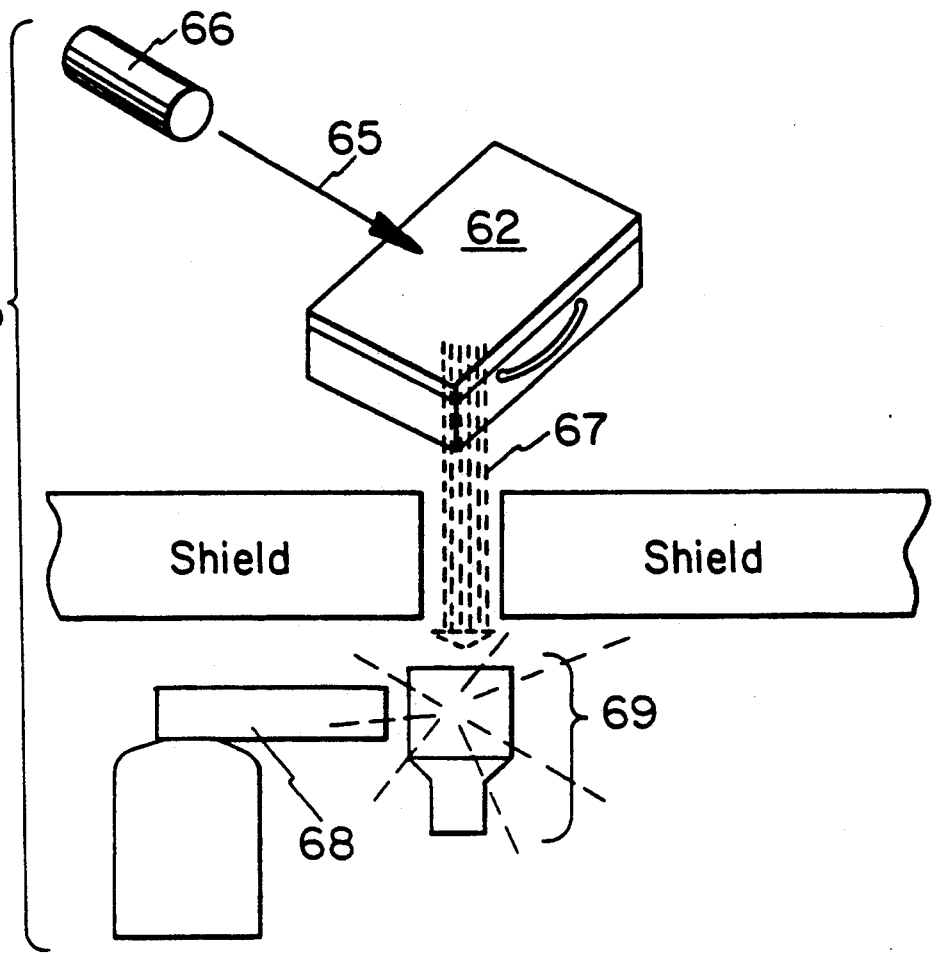
FIG. 6 is a schematic illustration of active nuclear fluorescence detection comprising an active NRF scatterer and a gamma detector, in accordance with the present invention.
Figure 7:
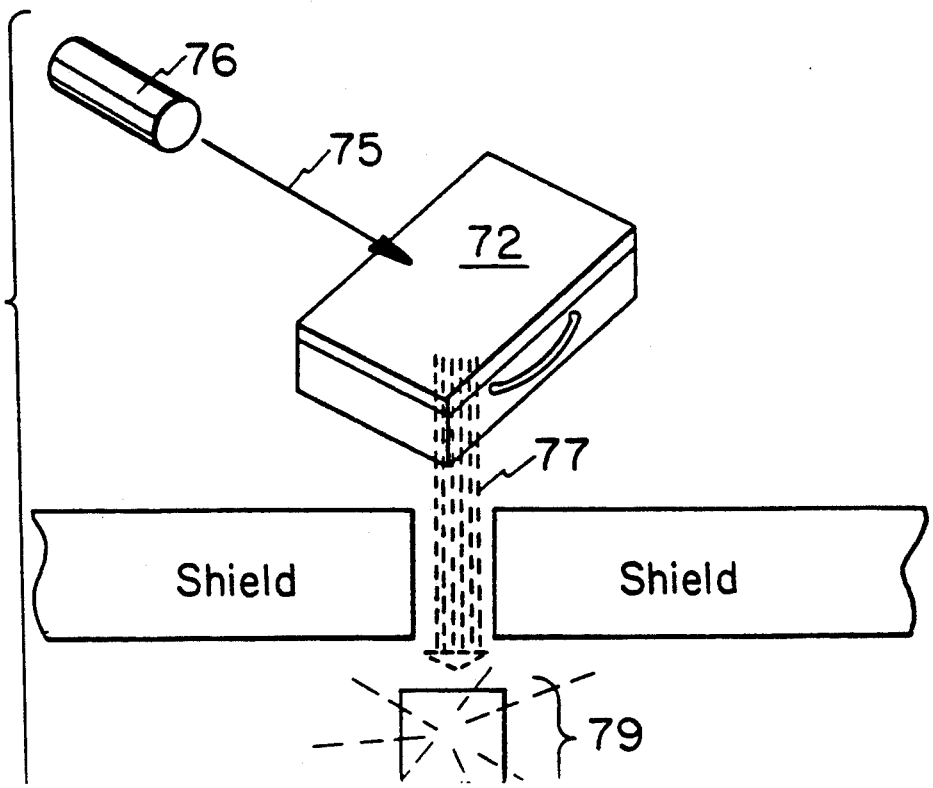
FIG. 7 is a schematic illustration of an active NRF detector comprising an active NRF scatterer within a gamma detector, in accordance with the present invention.

If the NRF scatterer indicates that scattering has taken place, i.e. operates as a radiation detector or a part of it, then it operates in an active mode. The energy selective detector of FIG. 6 utilizes an active NRF scatterer 69 and high resolution gamma detector 68. An additional example of an active mode is shown in FIG. 7, wherein resonant scattering nuclei are incorporated into the detector 79; either into a scintillator or into the gas, liquid or solid phase of a sufficiently sensitive radiation detector. The detector system of FIG. 6 for gamma-gamma analysis may also be employed in neutron activation analysis. The essence of the use of NRF in the radiation detector, whether active or passive, is the presence of nuclei having the same nuclear energy levels as energies of gamma rays to be detected. It is possible to use fortuitous energy coincidences, but such must be found in each particular case from a very large number of transitions. The method of use of NRF in a radiation detector is not dependent on finding such fortuitous coincidences, but on the following rules for particular cases of excitation:

a. For gamma rays originating from neutron capture in nucleus $^{A}M$, the proper resonant nucleus which should be present $Z$ in the passive or active NRF scatterer is that of

b. For gamma rays originating from nuclear resonance scattering, the investigated object,

there should be present in the NRF scatterer of the detector system nuclei

c. For gamma rays originating from inelastic scattering of neutrons or other particles on nuclei of

the NRF scatterer in the detector should contain nuclei of the same atomic number and mass, i.e.

d. In all cases in which charged particle resonance is used as a source of gamma rays, the NRF scatterer (detector) should contain nuclei of the same type as the transient compound nucleus formed in the interaction between the bombarding particle and the target.

If nuclear resonance scattering takes place within the active volume of the detector, a recoil takes place; and the recoiling nucleus produces a short track in the scintillator or ionization burst in the ionization detector. The energy of recoil is given by eq. (6); and for most practical cases, is of an order of a few KeV.

The special case of resonance take place if the energy of gamma photon interacting with the detector corresponds to the virtual level in the nucleus. In this case, an emission of a nucleon is energetically possible of particular consequence, is an emission of a charged particle, e.g. a proton. An example of such reaction particularly important in detection of nitrogen, is reaction $^{14}N(gamma, p)^{13}C$ with a photon corresponding to an energy of 9.17 MeV. Photons of this energy are produced in the $^{13}C(p,gamma)^{14}N$ reaction in an accelerator producing protons with energy of about 1.7476 MeV. The values of energies are such as available in the current reference sources. The actual values may undergo minuscule changes as the experiments are being made more accurate.

It can be easily seen that the reaction taking place in the NRF scatterer (detector) is the inverse of the reaction taking please in the original source of gamma rays, e.g. in the accelerator.

This can be illustrated in the case of detection of nitrogen $^{14}$N. If a target of $^{13}$C is bombarded with 1.7476 MeV protons, it produces gamma rays of energy of about 9.17 MeV. These gamma rays will be reasonably scattered by nuclei of $^{14}$N present in the analyzed sample; and in order to determine the amount of scattered radiation, an NRF detector will be used with nitrogen $^{14}$N present in the active volume of the detector. Some of the interactions between the incoming 9.17 MeV and nuclei of nitrogen in the detector will produce 1.7476 protons. An analogous situation may take place at other energies and other combinations of interacting particles and nuclei. The emitted particles could be, e.g. alpha particles.

The energy of recoil is given by eq. (6) and for most practical cases, is of an order of few keV. Such a heavy charged particle can be detected in a purpose designed detector and; originating from a heavy nuclei, may be discriminated against the electron background by one of known techniques, e.g. by rise time analysis. The same applies to the recoils of an interacting atom, mentioned earlier. The electron background is produced in Compton scattering interactions.

In addition to rise time discrimination, an energy discrimination of detected recoils and heavy-charged particle tracks may provide an identification of an elastic event. Only if the pulse from the detector fits into an energy window corresponding to a recoil in the active NRF scatterer, and its rise time is within time interval proper for the heavy recoiling nucleus, it could be assumed that a "resonant" photon has been scattered. In the systems that do not utilize the heavy charged particle signal in the scatterer, which may not be available in some types of excitation, then a use is made of the scattered-gamma rays from the active NRF scatterer into another gamma detector, the main detector, having high detection efficiency but without a high degree of energy selectivity. The proper selection of events is achieved by employing a coincidence between the recoil or heavy charged particle pulse from the active NRF scatterer and the pulse from the main detector, as shown in FIG. 6.

There is no limitation to the design and composition of the main detector. Particularly, scintillation detectors, proportional counters, solid-state detectors and multiwire proportional chambers are suitable for this application. The only requirement is that the rise time of the pulse produced by radiation in the main detector is sufficiently short to enable its use as one of the inputs to a coincidence circuit.

In some applications, it may be desirable to use the same photomultiplier 79 for both active NRF scatterer and for the main gamma ray detector, as shown in FIG. 7. The identification of events involving formation of a recoil track followed by detection of gamma quantum in the main detector can be achieved by means of a pulse shape analyzer which will permit seperate identification of both components of the light pulse. This can be done if the time constants of light pulses in both detectors, i.e. in the active NRF scatterer and in the main detector, are significantly different, as in the case of a plastic or liquid scintillator and an inorganic crystal.

In the prior art, the role of energy selector at the present state of radiation detector technology is played by pulse-amplitude discriminators, either in their simple forms or in a form of a multichannel analyzer. In the multichannel analyzer, the rate limiting step is analog-to-digital conversion. The effect of energy filtering is to reduce the counting rate before the conversion takes place. This reduction is a consequence of an introduction of an additional scattering stage in the form of the NRF scatterer into the process of detection. This process of scattering will much more profoundly affect the intensity of gamma rays detected off resonance than within the resonance. The filtration ratio, defined as an attenuation ratio of gamma-ray intensity at resonance energy to that off resonance, can be as high as 500–1000 times, for energies of gamma rays and nuclei levels perfectly matched. However, such match may be difficult to achieve and much lower filtration ratios are expected in practice. The width of the nuclear fluorescence resonance curve is usually much narrower than, the corresponding values for the resolution curves of the best available detectors.

An important feature of energy filtration of gamma rays in detection systems by means of Nuclear Resonance Fluorescence is that the filtration can be achieved for more than one level per nuclide, at the same time and in the same set up. For nuclides exhibiting multiple transitions and particularly closely spaced on energy scale transitions, the filtration can not be practically achieved by solely electronic means. Furthermore, the use of filtration by means of Nuclear Resonance Fluorescence can deal with many nuclides at the same time in the analyzed object. What is needed, is incorporation of appropriate nuclides into the NRF scatterer. There is no low-energy limit for passive filtration; but for an active filtration system, the limit is set by the noise and background level in the active NRF scatterer detector. In active systems with an NRF scatterer and a main detector when, due to the noise, the NRF scatterer detector can no longer furnish a reliable input to the coincidence system, the system may still be used in the same geometrical configuration as a passive system, with the consequent degradation of the degree of filtration. With an increasing atomic mass of the scatterer the energy of recoil is reduced; and again, the availability of sufficiently reliable input to the coincidence circuit limits application of active NRF filtering. The passive filtering remains unaffected.

Of particular interest is the use of nuclear resonance fluorescence in the detection of gamma rays in nuclear activation systems of the gamma-gamma type, which depends on the detection of resonantly scattered gamma rays from the investigated object. If the same nuclei which are being sought in the objects are present in the detector system, particularly but not exclusively, of the scintillation type, then the probability of interaction of these gamma rays with the scintillator is increased, owing to a much larger scattering cross section for gamma rays satisfying the condition of nuclear resonance.

Examples of such systems are scintillation detectors, gas or liquid ionization chambers and proportional counters, both single and multiple. The presence of resonant nuclei increases the probability of detection because it increases the absorption of resonant gamma rays in the scintillator. For instance, introduction into an organic scintillator of atoms of nitrogen will sensitize this scintillation to interactions with the gamma rays corresponding to nuclear levels in the same isotope of nitrogen.

An atom whose nucleus has absorbed a resonant photon, may undergo a process of internal conversion and emit an electron and/or a cascade of x-rays. The process of internal conversion following resonant excitation also contributes to an increased detection efficiency.

For the detection of nitrogen-based explosives in luggage, as shown in FIG. 1, the collimated beam from the accelerator is directed at the piece of luggage. The resonantly scattered radiation is observed at a large angle by means of energy selective radiation detectors, e.g. Ge(Li) or HPGe or NRF based detectors. A particular form of NRF detectors suitable for activation analysis for nitrogen are liquid scintillators containing nitrogen in either the primary or the secondary or ternary solute; but in general, any scintillator, solid or liquid, crystalline or not will be suitable as a detector. The simultaneous observation of resonant and non-resonant scattering (by observing the intensity of scattered beam at the resonance peak and off) permits detection of the presence of the sought element by measuring and, if desirable, displaying (e.g. the ratio of resonant to non-resonant signal). The intensity fluctuations in the beam must be considered when displaying the ratio.

The scanning of objects, such as luggage, will preferably be performed by a mechanical motion of the piece in respect of a stationary target and detector system. However, in principle it is possible to design a system in which the scanning is provided by non-mechanical displacement of the gamma illuminating beam spot on the surface of the luggage. One of the solutions is to have a strip target of adequate length and use the electrical or magnetic fields to displace the beam along it. The movement in a perpendicular direction can be provided by a mechanical displacement of the luggage. In the scanning mode, the resolution of the image depends upon the size of the beam. The scanning is, obviously, not limited to the checking of baggage, but can be used for industrial, medical and-investigation of art purposes.

The main advantage of the gamma-gamma system is that it does not practically induce radioactivity in the checked object as a result of resonant gamma-gamma scattering. The use of high-energy gamma rays for scanning nominally may induce radioactivity in some rarely met materials. It is unlikely that this induced activity would be detectable unless a very sensitive apparatus is used, and it will certainly be well below permitted levels of activity and of no health hazard at all. The luggage, after checking, can be immediately taken away by a passenger or luggage carrier. The gamma-gamma method can be used for most of the light elements and many of the medium and heavy ones.

In addition to inspection for the detection of explosives, luggage can be inspected for the detection of drugs which may be contained therein. In this embodiment, a ratio of different elements is employed, thereby, indicative of the presence of the drug of interest. Body composition may also be determined for applications in both medical and veterinary medicine. One of the uses of the gamma-gamma method is on-line control of composition of raw materials and manufactured products (particularly in situations where other monitoring systems, which may induce significant radioactivity) are not applicable. Quality control of food is accomplished by detection of the elements and also the ratio of elements contained in said food.

In order to assure correct and reliable operation of the gamma-gamma system, it is necessary to stabilize energy of the particle beam and to know the intensity of the photon beam before it strikes the investigated object. Furthermore, it is important to know the "active fraction" of the photon beam, i.e. the part of the total photon flux which is scattered resonantly from the nuclei of interest.

While illustrative embodiments of the subject invention have been described and illustrated, it is obvious that various changes and modifications can be made, therein, without departing from the spirit of the present invention which should be limited only by the scope of the appended claims.

We claim:

1. An apparatus for scanning an object to determine the concentration of an element of interest in the object comprising:
   means for producing primary gamma rays of required energy to be resonantly scattered by the element to be detected, said means for producing gamma rays includes an accelerator providing hydrogen or heavier ions directed at a target thereby producing excited atoms of the elements of interest which deexcite and provide a beam of gamma rays of the required energy to be resonantly scattered by the element of interest;
   means for stabilizing the intensity and energy of said beam of gamma rays;
   means for positioning said object within the beam of gamma rays;
   means for detecting the resonantly scattered gamma rays and for producing output signals representative of the energy of said resonantly scattered gamma rays; and
   means for processing and analyzing said output signal for determining the amount of the element of interest.

2. The apparatus of claim 1 wherein said element of interest is $^{14}N$.

3. The apparatus of claim 2 wherein said accelerator provides hydrogen ions and said target is $^{13}C$.

4. The apparatus of claim 2 wherein said accelerator provides deuterium ions and said target is $^{12}C$.

5. The apparatus of claim 1, 3 or 4 wherein said means for detecting the scattered gamma rays is positioned at an angle greater than 90 degrees from the axis of bombardment at which the primary gamma rays interact with the object.

6. The apparatus of claim 5 which further includes
   means for detecting the non-resonantly-scattered gamma rays and for producing output signals representative of the energy of the non-resonantly scattered gamma rays;
   means for processing and analyzing said non-resonant output signals; and
   means for generating a ratio of resonant to non-resonant output signals.

7. The apparatus of claim 6 wherein said means for generating a ratio includes a means of displaying said ratio.

8. The apparatus of claim 1 wherein said means for detecting the scattered gamma rays includes a liquid scintillator and a high-resolution detector.

9. The apparatus of claim 8 wherein the high-resolution detector is a Ge(Li) or HPGe detector.

10. The apparatus of claim 1 wherein the accelerator is an electrostatic accelerator or a radio-frequency-quadrupole accelerator.

11. The apparatus of claim 1 wherein the means for positioning includes means for transporting the object through the beam of gamma rays.

12. The apparatus of claim 11 wherein said means for positioning includes a conveyor means for introducing said object to be scanned into said means for transporting said object through said beam of gamma rays.

13. The apparatus of claim 1 for scanning an object to determine the presence and concentration of two or more elements of interest in said object wherein said accelerator includes an electronic voltage adjustment and a control beam for striking two or more targets.

14. The apparatus of claim 1 or 13 wherein said element of interest includes a first and second element of interest within a drug and said means for producing primary gamma rays includes a first and second means for producing primary gamma rays of the required energy to be resonantly scattered by the first and second element to be detected.

15. The apparatus of claim 1 wherein the means for detecting the scattered gamma rays includes an energy-filtering element.

16. The apparatus of claim 15 wherein the energy-filtering element is in a passive mode.

17. The apparatus of claim 15 wherein the energy-filtering element is in an active mode.

18. The apparatus of claim 1 wherein the detecting means is selected from the group consisting of scintillation detector, proportional counter, solid-state detector, and multiwire-proportional chamber.

19. The apparatus of claim 1 wherein said means for stabilizing the gamma ray beam intensity and energy comprises:
  means for detecting said gamma-ray beam prior to scattering and producing second output signals representative of the beam intensity and energy;
  means to split said beam of gamma rays thereby providing a primary and secondary beam of gamma rays;
  a reference scatterer positioned within said secondary beam of gamma rays;
  means for detecting the resonantly scattered gamma rays from said reference scatterer and producing third output signals representative of the energy of the resonantly scattered gamma rays from the reference scatterer; and
  means for processing and analyzing said second and third output signals for determining the stabilization of the gamma ray beam intensity and energy.

20. The apparatus of claim 1 wherein said element of interest is a plurality of elements of interest and said means for producing primary gamma rays includes a plurality of means for producing primary gamma rays of the required energy to be resonantly scattered by the elements to be detected.

21. A method of scanning an object for an element of interest in the object, comprising:
  accelerating hydrogen or heavier ions detected toward a target to produce excited atoms of the element of interest, said excited atoms deexciting to provide a beam of primary gamma rays of the required energy to be resonantly scattered by the element of interest within the object; said primary gamma rays directed toward the object;
  stabilizing the intensity and energy of said beam of gamma rays;
  positioning said object within said beam of primary gamma rays;
  detecting the resonantly scattered gamma rays and producing output signals representative of the energy of said gamma rays; and
  analyzing said output signals to determine the concentration of the element of interest.

22. The method of claim 21 which further includes:
  accelerating hydrogen or heavier ions towards a plurality of targets to produce excited atoms of a plurality of elements within said object to provide a plurality of primary gamma rays of the required energy to be resonantly scattered by the elements; and
  analyzing said output signals to determine the ratio of the concentration of the plurality of elements within the object.

23. A method of scanning an object for nitrogen in the object, comprising:
  accelerating hydrogen or deuterium ions directed toward $^{12}C$ or $^{13}C$ to produce excited atoms of nitrogen, said excited atoms deexciting to provide primary gamma rays of the required energy to be resonantly scattered by the nitrogen within the object; said primary gamma rays directed toward the object;
  stabilizing the intensity and energy of said beam of gamma rays;
  positioning said object within said beam of gamma rays;
  detecting the resonantly scattered gamma rays and producing output signals representative of the energy of said gamma rays; and
  analyzing said output signals to determine the concentration of the nitrogen.

24. The method of claim 21 or 22 which further includes:
  detecting the non-resonantly scattered gamma rays and producing output signals representative of the energy of the non-resonantly scattered gamma rays;
  processing and analyzing said non-resonant output signals; and
  generating a ratio of resonant to non-resonant output signals.

25. The method of claim 24 wherein generating a ratio includes displaying said ratio.

26. A method of scanning an object for a drug of interest within said object comprising:
  accelerating hydrogen or heavier ions directed toward a target to produce excited atoms of an element within the drug of interest, said excited atoms deexciting to provide a beam of primary gamma rays of the required energy to be resonantly scattered by the element; said beam of primary gamma rays directed toward the object;
  stabilizing the intensity and energy of said beam of gamma rays;
  positioning said object within said beam of primary gamma rays;
  detecting the resonantly scattered gamma rays and producing output signals representative of the energy of said resonantly scattered gamma rays; and
  analyzing said output signals to determine the concentration of the element within the object.

27. The method of claim 26 which further includes:
  accelerating hydrogen or heavier ions toward two targets to produce excited atoms of two elements within the drug of interest to provide two primary gamma rays of the required energy to be resonantly scattered by the two elements; and analyzing said output signals to determine the ratio of the concentration of the two elements within the object.

28. The method of claims 21, 23 or 26 wherein the stabilizing step includes:

detecting said gamma ray prior to scattering and producing second output signals representative of the beam intensity and energy;

splitting said beam of gamma rays thereby providing a primary and secondary beam of gamma rays;

positioning a reference scatterer within said secondary beam of gamma rays;

detecting the resonantly scattered gamma rays from said reference scatterer and producing third output signals representative of the energy of the resonantly scattered gamma rays from the reference scatterer; and processing and analyzing said second and third output signals for determining the stabilization of the gamma ray beam intensity and energy.

* * * * *

UNITED STATES PATENT AND TRADEMARK OFFICE
CERTIFICATE OF CORRECTION

PATENT NO. : 5,293,414
DATED : March 8, 1994
INVENTOR(S) : Kamil V. Ettinger, et al.

It is certified that error appears in the above-indentified patent and that said Letters Patent is hereby corrected as shown below:

Column 2, line 65: "Scaltering" should read --Scattering--

Column 4, line 41: "thug" should read --thus--

Column 6, line 33: "mind-that" should read --mind that--

Column 13, line 39: "and-investigation" should read --and investigation--

Column 15, line 58, Claim 21: "detected" should read --directed--

Signed and Sealed this

Fourteenth Day of February, 1995

Attest:

BRUCE LEHMAN

*Attesting Officer*  *Commissioner of Patents and Trademarks*